United States Patent [19]

Weaver

[11] Patent Number: 5,169,776
[45] Date of Patent: Dec. 8, 1992

[54] METHOD TO OBTAIN INTACT, VIABLE PROTOPLASTS FROM POLLEN GRAINS

[75] Inventor: Merle L. Weaver, Martinez, Calif.

[73] Assignee: The United States of America as represented by the Secretary of Agriculture, Washington, D.C.

[21] Appl. No.: 59,988

[22] Filed: Jun. 9, 1987

[51] Int. Cl.⁵ .................. C12N 5/02; C12N 5/00
[52] U.S. Cl. .................. 435/240.47; 435/240.45; 435/240.54
[58] Field of Search ............ 47/58; 435/240.4, 240.47, 435/240.45, 240.54

[56] References Cited

PUBLICATIONS

Weaver et al. (1986) Hortscience 21(3):164, Abstr. #416.
Bajaj (1983) in *International Rev. Cytol.* Suppl. 16, G. H. Bourne et al., eds., Academic Press. N.Y., p. 114.
Evans et al., (1983) in *Handbook of Plant Cell Culture*, vol. 1, D. A. Evans et al., eds., Macmillan Publ. Co., N.Y., pp. 129 and 136.
Hawley (1981) *The Condensed Chemical Dictionary*, 10th Ed., Van Nostrand Reinhold Co., N.Y., p. 492.
Linskens, H. 1963, p. 143 In: Pollen physiology and fertilization, North-Holland Publishing Co., Amsterdam.
Bengochea et al., 1986, Plant protoplasts, p. 8, Chapman and Hall, New York.
Evans et al., 1983, Handbook of plant cell culture vol. 1, Macmillan Publishing Co., New York, pp. 125-128.
Pilet, P. 1972, Experientia 28:638-639.
Pilet, P. 1973, Experientia 29:10-11.
Rosen, W. 1968, p. 435 In: Ann. Rev. Plant Physiology, vol. 19, Annual Reviews, Inc., Palo Alto, CA.
Y. P. S. Bajaj (1977) "Protoplast Isolation, Culture, and Somatic Hybridization," in J. Reinert and Y. P. S. Bajaj, eds., Applied and Fundamental Aspects of Plant Cell, Tissure, and Organ Culture, pp. 469-474).
Ray et al. (1983) Botany, Saunders College Publishing, NY, pp. 153-155.
K. Esau (1967) Plant Anatomy, Second Edition, John Wiley and Sons, Inc., NY, pp. 553-554.
E. C. Cocking, "Plant Cell Protoplasts—Isolation and Development," *Annual Review of Plant Physiology* 23:29-50 (1972).
B. G. Baldi, V. R. Fransceschi, and F. A. Loewus, "Pollen Sporoplasts," *Plant Physiology* (Suppl.) 77(4): 71 (1985).
R. G. S. Bidwell, "Flowers and Fruit,"*Plant Physiology*, Macmillan Publishing Co, Inc., New York, pp. 81-84 (1974).

*Primary Examiner*—David T. Fox
*Attorney, Agent, or Firm*—M. Howard Silverstein; John D. Fado; Margaret A. Connor

[57] ABSTRACT

Intact, viable protoplast are obtained readily and in good quantity from within the cell walls of mature pollen grains. Pollen grains are contacted with an aqueous medium containing an osmolyte, gelatin, or a combination thereof in a concentration to expand the protoplast and force it out through the pore in the cell wall of the pollen grain, while maintaining the protoplast intact and viable.

21 Claims, 1 Drawing Sheet

METHOD TO OBTAIN INTACT, VIABLE PROTOPLASTS FROM POLLEN GRAINS

BACKGROUND OF THE INVENTION

1. Field of the Invention

The present invention relates to and has among its objects the provision of a novel method to obtain intact, viable plant protoplasts from within the cell walls of mature pollen grains.

2. Description of the Art

Pollen is unique among higher plant cells. It is haploid, that is, it has the number of chromosomes present in the normal reproductive cell which is equal to half the number in the normal somatic cell (cells that become differentiated and compose the tissues, organs, and parts of the individual plant). Each pollen grain is a single cell; it grows singly in culture behaving like a unicellular organism, unconfined by neighboring cells.

Pollen grains of flowering plants are usually spherical, elipsoid, or fusiform in shape. In its most basic form, a mature pollen grain has an inner protoplast cell surrounded by a protoplast membrane and an outer compound cell wall which is made up of an inner pectocellulosic layer, the intine, and an outer layer of sporollenin, the exine. The exine is characterized as a polymer of carotenoids and carotenoid esters and is highly resistant to biodegradation. One of the major functions of the cell wall is to prevent overexpansion, e.g., through uptake of water, of the protoplast with consequent rupture of the protoplast cell. Located in the cell wall are, in most cases, one or more small thinner walled areas, called pores, which represent positions of possible emergence of pollen tubes.

The protoplast represents the totality of living cell constituents. Protoplasts which have been obtained from within cell walls are capable of growing and dividing. Because of this, protoplasts have many important uses. One of the most important uses is the production of hybrid plants by somatic hybridization. For example, intra- and inter-generic or intra- and inter-specific plants can potentially be produced by hybridization. This is of particular value in those instances where sexual incompatibilities prevent such crosses by conventional pollination procedures. Other uses of isolated protoplast cells include: regeneration of new plants from a single cell; incorporation of genetic material into the cell; investigation of structural, physiological, and genetic alterations; elucidation of details of cell structure and function; and studies of plant virus infections and uptake of macromolecules by protoplasts.

In the isolation of plant protoplasts, an essential criterion is that release of the protoplast is obtained without causing irreversible damage to the protoplast. Of primary importance is the fact that protoplasts are osmotically active and will, under conditions of low or high osmotic potential, take up or lose water. When the cell wall (which exerts a wall pressure on the protoplast) is removed, it is critical that overexpansion and rupture of the cell caused by excessive uptake of water is prevented. Conventional methods to isolate protoplasts from plant tissue in general, e.g., leaf mesophyll cells, callus cells and the like include (1) mechanical cutting of the cell wall, (2) enzymatic degradation of the cell wall, and (3) use of solvents to dissolve the cell wall.

In the mechanical method, plant cells are placed in a plasmolyzing solution, e.g., calcium chloride or calcium nitrate (0.25 or 0.3M) or sucrose (1.0M), to shrink the protoplast away from the cell wall; then the wall is cut with a sharp knife. In some cases, a thin slice of the cell wall is cut and then the solution is changed to 0.5M sucrose to cause the protoplast to expand and force it through the cut surface. The major disadvantages of this method are that it is time consuming and the number of intact, undamaged protoplasts which can be removed by this by this method is few. Only those protoplasts in which marked plasmolysis and good separation of the protoplast from the cell wall occur can be successfully released from the cell wall using this method.

In the enzymatic method for the isolation of protoplasts, plant tissue, e.g., leaf mesophyll cells, are incubated with enzymes which free the cells, and the cells are treated with cell-degrading enzymes such as pectinase, cellulase, hemicellulase, or combinations thereof, to break down the cell wall and release the protoplast. While large quantities of released protoplasts can be obtained from leaf mesophyll tissue or callus tissue by this method, it has the disadvantage that substances in the crude enzyme preparation, e.g., proteases, lipases, perioxidases, and ribonucleases, can damage the protoplast or destroy the functional compounds in the protoplast membrace surface. Since the usefulness of the protoplasts is in their culture and further manipulation, it is essential that any adverse effect of the enzymes be minimized.

In the solvent method for the release of plant protoplasts, cell-degrading solvents, e.g., 4-methylmorpholine N-oxide monohydrate, are used to dissolve the cell wall. This is done at high temperatures (ca., 70° to 80° C.). The main disadvantage of this method is that damage to the protoplast can result from these strong solvents and the high temperature that has to be used.

With regard to mature pollen grains, the major difficulty encountered in release of protoplasts from the cell wall is the presence of the durable and highly resistant substance, sporopollenin, in the exine. Although, it is possible to partially degrade the exine through treatment with mixtures of cell wall-degrading enzymes, only limited quantities of protoplasts have been obtained by this method. Of major concern in the isolation of pollen protoplasts by this method is the potential harmful effects of the enzymes on the protoplasts. Mechanical isolation of protoplasts from pollen grains results in only limited numbers of protoplasts, and isolation of pollen protoplasts using solvent has the potential of damaging the protoplasts. In view of the potential usefulness of pollen protoplasts for use in somatic cell hybridization; regeneration of haploid plants; uptake of small and large molecules, viruses, bacteria, chloroplasts, DNA, and whole nuclei; and studies of mutation and cell modification, a method to readily obtain intact, viable protoplasts from within the cell walls of mature pollen grains is of great importance.

SUMMARY OF THE INVENTION

The invention provides a novel method for nondestructive release of plant protoplasts from within the cell walls of mature pollen grains. With the invention, large quantities of intact, viable plant protoplasts can be obtained while avoiding the disadvantages of the prior art methods.

The method of the invention comprises placing mature pollen grains in an aqueous medium which contains an additive in an effective amount to cause movement of water from the aqueous medium into the protoplast to expand the protoplast and force it out through the pore in the cell wall of the pollen grain, while maintaining the protoplast intact and viable.

In one embodiment of the invention, mature pollen grains are placed in an aqueous medium containing an osymolyte in a concentration sufficient to rapidly expand the protoplast and force it out through the pore in the cell wall. In another embodiment, gelatin is used as the protoplast expanding agent. In a third embodiment, gelatin and an osmolyte are used together in the aqueous medium.

In accordance with this discovery it is an object of the invention to provide means to obtain intact, viable plant protoplasts from within the cell walls of mature pollen grains readily and in good quantity.

Another object of this invention is to provide a nonenzymatic and nondestructive method to release protoplasts from within pollen grains.

It is a further object to provide a method for obtaining plant protoplasts for a multitude of uses, for example, for regenerating new plants from a single cell; for fusing protoplasts to create interspecific crosses that could not be created by standard breeding techniques, and for fusing two protoplasts of the same species.

Other objects and advantages of the invention will become readily apparent from the ensuing description.

DETAILED DESCRIPTION OF THE INVENTION

Figure 1:
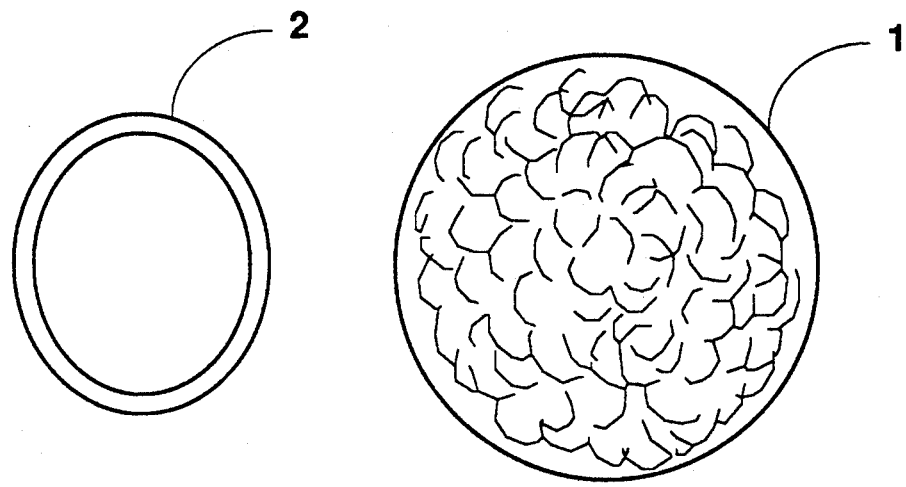
FIG. 1 shows release of a protoplast from within the cell wall of a pollen grain by the method of the invention wherein the entire protoplast has been forced outside of the cell wall.

The method of the invention comprises contacting mature pollen grains with an aqueous medium containing an effective amount of an additive which causes the protoplast to expand and force it out through the pore in the cell wall of the pollen grain while maintaining the protoplast intact and viable.

The critical feature of the invention is that the additive in the aqueous medium is of a type and in a concentration to cause the movement of water from the aqueous medium containing the additive to the protoplast to effect controlled expansion of the protoplast, that is, sufficient expansion to force the protoplast out through the pore in the cell wall of the pollen grain but insufficient to burst the protoplast.

In one embodiment of the invention, the protoplast expanding agent is an osymolyte. Typical osmolytes include salts of sodium, potassium, and magnesium. The anion component of the salt is not critical except that it must be one that is compatible with maintaining the viability of the protoplast. Typical anions include chloride, nitrate, lactate, citrate, and the like. Concentration of the osmolyte in the aqueous medium must be sufficiently dilute to expand the protoplast and force it out through the pore in the cell wall and sufficiently concentrated to prevent the protoplast from overexpanding and bursting. The effective range of concentration is 0.005 to 0.2M, preferably 0.02 to 0.08M. In an alternate embodiment, gelatin is used as the protoplast expanding agent. The effective concentration of gelatin in the aqueous medium is 1% to 20%, preferably 6% to 12%. In a third embodiment, gelatin and an osmolyte are used together in the aqueous medium in the concentration ranges for each agent when used alone.

The unique character of the invention is illustrated by the fact that the following additives were not effective alone for obtaining protoplasts from mature pollen grains: glucose, lactose, dextrose, sucrose, galactose, myo-inositol, mannitol, mannose, sorbitol, dextrin, polyethylene glycol, soluble starch, hydroxyethylcellulose, lecithin, or agarose. It should be noted that while water causes expansion of pollen protoplasts, it is not controlled expansion and most of the protoplasts rupture.

In carrying out the method of the invention, the pH of the medium containing the protoplast expanding agent must be compatible with maintaining the viability of the protoplast. For osmolytes, the pH is maintained at 5 to 10, preferably 6 to 9. For gelatin, the pH is maintained at 5 to 9, preferably 6 to 7. The temperature must also be compatible with maintaining the viability of the protoplast. This will vary somewhat with the species of plant. In general, for osmolytes the temperature range is about 1.65° C. to 38° C. An additional constraint for gelatin is that the temperature is not so high as to cause the gelatin to melt or otherwise adversely effect the gelatin. For gelatin, the effective temperature range is 20° C. to 30° C., preferably 23° C. to 27° C. When gelatin and an osmolyte are used together, the pH and temperature of the medium are maintained as described for gelatin alone.

Other materials may be added to the aqueous medium containing the protoplast expanding agent. In one case, agar is added to the osmolyte-containing medium in a concentration range of about 0.5% to 4%. Other materials which may be added include materials which stabilize protoplasts, for example sucrose, mannitol, sorbitol, and the like; and minerals of a type and in a concentration compatible with the viability of protoplasts such as calcium, magnesium, potassium, manganese, boron, and the like. Typical concentration ranges are as follows: 1 to 25% protoplast stabilizer, and 10 to 400 ppm of a mineral salt.

The method of the invention is useful to release protoplasts from within the cell walls of mature pollen grains. For all flowering plants, pollen grains obtained from freshly opened flowers are considered mature pollen grains for the purposes of this invention. In the case of the common bean, pollen grains obtained from flower buds at the late white-petal stage (keel just beginning to split) work in a smaller percentage of cases and are not preferred. For other plants, pollen grains selected at this equivalent stage of maturity are also not preferred. Pollen grains obtained from flower buds of the common bean at the early white-petal stage (keel tight) are not sufficiently mature for the purposes of this invention. Again, for other plants, pollen grains of the equivalent stage of maturity are not sufficiently mature for the invention.

Figure 2:
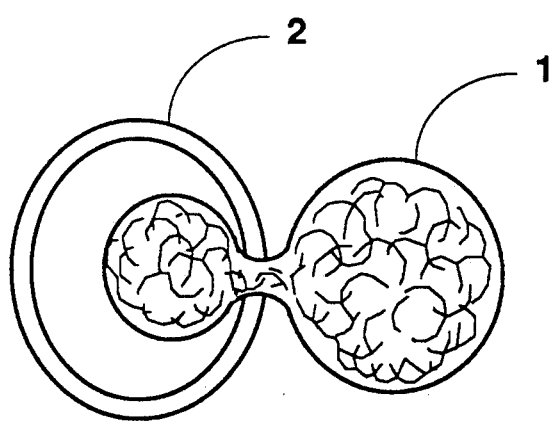
FIG. 2 shows release of a protoplast from within the cell wall of a pollen grain by the method of the invention wherein the protoplast has been partially forced outside the cell wall.

The phrase "force the protoplast out through the pore in the cell wall" as used herein encompasses the following: (1) the entire protoplast is forced outside of the cell wall and is entirely free of the cell wall (FIG. 1); (2) the protoplast is partially forced through the pore and is partially outside of the cell wall (FIG. 2); or (3) both (1) and (2). In FIGS. 1 and 2, the protoplast is denoted by numeral 1 and the cell wall by numeral 2.

Protoplasts which are entirely outside or partially outside of the pollen grain cell wall are useful for many purposes as described above. For some uses, there are advantages in having the protoplast only partially out of the pore. For example, for carrying out fusion between protoplasts, it may be an advantage to work with partially free protoplasts as the cell wall would not be floating free in the medium and thus could not get in the area of fusion between the protoplasts. Also, it appears from observation under the microscope that partially free protoplasts are less susceptible to damage during movement in the medium than protoplasts that are entirely free of the cell wall. Because only a small area of protoplast free of the cell wall is necessary for incorporation of genetic material, another important use for partially released protoplasts is for incorporation of DNA and the like into the protoplast.

The method to obtain intact, viable protoplasts from mature pollen grains using osmolytes works best with the common green bean (*Phaseolus vulgaris L.*). Protoplasts from bean pollen can be used to make interspecific crosses with protoplasts from pollen obtained by the method described herein or from protoplasts from plant pollen or leaf mesophyll cells obtained by standard techniques. Intact, viable bean protoplasts are obtained rapidly (within 5 minutes) and in good quantity, greater than 80% in many cases, using dilute aqueous solutions of osmolytes in accordance with the invention. The method is illustrated in detail below in Examples 1-4. This method is also useful for obtaining small quantities of protoplasts from cowpea and lima bean pollen grains, generally about 1-2%. Use of osmolytes is not useful for obtaining tomato, pepper, cucumber, or zucchini protoplasts from pollen.

Gelatin has been found to provide intact, viable protoplasts from within the cell wall of mature pollen grains for every species of plant pollen tested. For example, as described in detail below in Example 5, when gelatin is used in accordance with the method of the invention, intact, viable protoplasts which are forced at least partially out of the cell wall are obtained from cowpea, pea, tomato, lima bean, cucumber, and pepper pollen. When gelatin is used, the protoplasts are forced out through the pore in about 1 to 18 hours.

As shown in Example 6, the combination of gelatin and an osmolyte in the aqueous medium is also effective in expanding the protoplast and forcing it out through the pore in the cell wall of mature pollen grains while maintaining the protoplast intact and viable.

After the protoplasts are forced entirely or partially out of the cell wall, they are used in situ or separated from the medium by conventional techniques such as filtration or centrifugation. Cell wall debris in the medium may be separated from the protoplasts by conventional techniques such as filtering.

Protoplasts obtained by the method of the invention find many uses. For example, they can be placed in a regeneration medium to get cell division and new platelets; placed in fusion medium for somatic hybridization with protoplasts of the same species or different species to develop inter- and intra-specific plants; or placed in medium suitable for growth and development. (See E. C. Cocking, *Ann. Rev. Plant Physiol.* 23: 29-50 (1972)).

EXAMPLES

The following examples are intended only to further illustrate the invention and are not intended to limit the scope of the invention which is defined by the claims.

COLLECTION OF POLLEN GRAINS

Mature pollen grains were obtained as follows: plants were grown in the greenhouse in a commercial potting mix which provided all the nutrients essential for growth in 20 cm clay pots at 25° C./21° C. (D/N), with a photoperiod of 14 h/10 h (D/N). Freshly opened flowers were collected and denoted as mature pollen grains. The pollen grains were generally used for protoplast release within about 5 to 30 minutes after collection.

EXAMPLE 1

Pollen was obtained from the common green bean (*Phaseolus vulgaris* L. cv. 'Monroe') as described above. Pollen from an individual flower was shaken into the well of a 7.62×2.54 cm microconcavity slide. Two drops of a dilute aqueous solution containing the osmolyte were placed on the pollen and covered with a cover slide. The osmolytes used were sodium chloride and potassium chloride. Solutions having a concentration of 0 to 0.16M NaCl and 0 to 0.10M KCl were tested. The pH of the solutions was 6.0. Tests were carried out at ca. 25° C. Protoplasts were determined as total (combined number of protoplasts which were either entirely or partially forced outside of the cell wall out of 100 observed pollen grains), free (number of protoplasts forced entirely outside of the cell wall out of 100 observed pollen grains), or partial (number of protoplasts forced partially out of the cell wall out of 100 observed pollen grains). Each test was repeated 6 times using a minimum of 12 flowers for each of 3 replications. The mean for each value was determined using a minimum of 500 pollen grains from each flower. All data were statistically evaluated and means compared using Duncan's Multiple Range test (P=0.05) (G. W. Snedecor, *Statistical Methods*, Iowa State University Press, Ames, Iowa (1956)). Viability of released protoplasts was determined using 0.1% methylene blue (L. M. Vairo, "Methylene Blue Solutions for Staining Dead Yeast Cells," *Stain Technology* 36: 329-330 (1961)) and fluorescein diacetate (H. Y. Young, "Fluorescein Diacetate Used as a Vital Stain for Labeling Living Pollen Tubes," *Plant Science* 44: 59-63 (1986)). Protoplast release was microscopically determined at 100×15 minutes after addition of the dye solution. The results are shown in Table 1. In a 0.03M NaCl solution at pH 6.0, protoplast release began within 45 to 60 seconds and was complete for over 80% of the pollen grains within 5 minutes. Sodium chloride and potassium chloride were found to be equally effective for protoplast release. At 0.01M NaCl, protoplast release occurred from about 91% of the pollen grains, but in over one-third only partial release was accomplished. From 0.02M through 0.06M NaCl protoplast release occurred for about 90% of the pollen grains, and over 90% of these were totally released from the cell wall. As molarity increased from 0.07 to 0.1M, the number of total (free and partial) protoplasts and the number of free protoplasts decreased, while the number of partial protoplasts increased. The release response for KCl solutions was almost identical to that of a NaCl solutions of the same molarity. As the concentration of the salt was increased above 0.02M, protoplast release was reduced from 89% at 0.02M to 45% at 0.1M. Bean pollen placed in water alone without an osmolyte rapidly expanded but most protoplasts ruptured.

TABLE 1

| Salt (M) | Protoplast Release (%) | | |
|---|---|---|---|
| | Total | Free | Partial |
| NaCl | | | |
| 0 (H₂O Control) | 20d | 20e | 0 |
| 0.01 | 91a | 68b | 23c |
| 0.02 | 90a | 85a | 5f |
| 0.03 | 87a | 82a | 5f |
| 0.04 | 91a | 85a | 6f |
| 0.05 | 90a | 83a | 7f |
| 0.06 | 92a | 84a | 5f |
| 0.07 | 80b | 70b | 10ef |
| 0.08 | 75b | 60c | 15de |
| 0.09 | 75b | 40d | 35b |
| 0.10 | 50c | 0 | 50a |
| 0.13 | 20d | 0 | 20c |
| 0.16 | 3e | 0 | 3f |
| KCl | | | |
| 0.01 | 89a | 66b | 23b |
| 0.02 | 88a | 85a | 3d |
| 0.04 | 87a | 82a | 5d |
| 0.06 | 85a | 79a | 6d |
| 0.08 | 70b | 55c | 15c |
| 0.10 | 45c | 0 | 45a |

[1]Means in the same column followed by the same letter are not significantly different using the Duncan's Multiple Range test.

For comparison purposes, bean pollen was contacted with dilute aqueous solutions of calcium chloride. The results are shown in Table 2. No protoplasts were released from the pollen grains.

TABLE 2

| Salt (M) | Protoplast Release (%) | | |
|---|---|---|---|
| | Total | Free | Partial |
| CaCl₂ | | | |
| .0015 | 0 | 0 | — |
| .003 | 0 | 0 | — |

The effect of pH on protoplast release was investigated. The results are shown in Table 3. Solutions of 0.01M NaCl having the pH controlled from 5.0 to 9.0 with 1.0N HCl or 1.0N KCl were used to obtain protoplasts from bean pollen. At pH 5.0, 65% of the protoplasts were released from within the cell walls of the pollen grains; of these, 25% were entirely free of the cell wall and 40% were partially free. In solutions of pH 6.0 to pH 9.0, almost all protoplasts released were entirely free from the cell wall. In a 0.03M NaCl solution at pH 6.0 protoplast release began within 45 to 60 seconds and was completed for over 80% of the pollen grains within 5 minutes.

TABLE 3

| pH | Protoplast Release (%) | | |
|---|---|---|---|
| | Total | Free | Partial |
| 5.0 | 65c[1] | 25c | 40a |
| 6.0 | 95a | 90a | 5b |
| 7.0 | 88ab | 84ab | 4b |
| 8.0 | 89ab | 85ab | 4b |
| 9.0 | 83b | 80b | 3b |

[1]Means in the same column followed by the same letter are not significantly different using the Duncan's test.

EXAMPLE 2

Bean pollen obtained as described in Example 1 was treated with dilute solutions of sodium chloride at pH 6.0 having 0.5% and 1.0% bacto-agar (Difco Laboratories, Detroit, Mich.) added to the salt solution. The agar-salt gel was placed in 100 mm diameter petri dishes (about 4 cm layer). Pollen was shaken onto the agar, topped with a coverglass, and evaluated for protoplast release as described in Example 1. The replication procedure was the same as described in Example 1. The results are shown in Table 4. Percentage of pollen releasing protoplasts (total) was similar at either agar concentration used and at all salt concentrations from 0.005M to 0.08M. The percentage of free protoplasts, however, increased at either agar level as the salt concentration increased. At similar salt concentrations, the percentage of partially free protoplasts was highest when using 1.0% agar for solidification. Protoplast release for over 80% of the pollen grains was completed in about 5 minutes.

TABLE 4

| NaCl (M) | Agar (%) | Protoplast Release (%) | | |
|---|---|---|---|---|
| | | Total | Free | Partial |
| 0.005 | 0.5 | 85a[1] | 25d | 60b |
| 0.01 | 0.5 | 81a | 45c | 40c |
| 0.02 | 0.5 | 82a | 60b | 22d |
| 0.04 | 0.5 | 79a | 68a | 11e |
| 0.005 | 1.0 | 80a | 5f | 75a |
| 0.01 | 1.0 | 87a | 7f | 80a |
| 0.02 | 1.0 | 86a | 18e | 67b |
| 0.04 | 1.0 | 81a | 16e | 65b |
| 0.06 | 1.0 | 86a | 50c | 36c |
| 0.08 | 1.0 | 79a | 44c | 35c |

[1]Means in the same column followed by the same letter are not significantly different using the Duncan's Multiple Range test.

EXAMPLE 3

The effect of the osmotic stabilizer sucrose on the release of bean protoplasts in dilute sodium chloride solutions was evaluated. The results of 0 to 40% sucrose addition to 0.03M NaCl and of 1 to 5% sucrose, without NaCl on bean pollen obtained as described in Example 1 are shown in Table 5. Sucrose, in the absence of sodium chloride did not cause protoplast release. Addition of 1% to 10% sucrose to the salt solution, however, significantly improved the release of bean protoplasts, almost all of which were entirely free of the cell wall. As the sucrose content was increased to 15% or greater, both the total number of protoplasts released and percentage of totally free protoplasts were decreased, and the number of partially released protoplasts was increased.

TABLE 5

| | Sucrose (%) | Protoplast Release (%) | | |
|---|---|---|---|---|
| | | Total | Free | Partial |
| With 0.03M NaCl | 0 (Control) | 80b[1] | 78b | 2e |
| | 1 | 90a | 87a | 3e |
| | 3 | 92a | 88a | 4e |
| | 5 | 90a | 86a | 4e |
| | 10 | 88a | 85a | 3e |
| | 15 | 80b | 75b | 5e |
| | 20 | 75b | 50c | 25d |
| | 25 | 76b | 41d | 35c |
| | 30 | 75b | 25e | 50b |
| | 40 | 71b | 11f | 60a |
| Without 0.03M NaCl | 1 | 0 | 0 | — |
| | 3 | 0 | 0 | — |
| | 5 | 0 | 0 | — |

[1]Means in the same column followed by the same letter are not significantly different using the Duncan's Multiple Range test.

EXAMPLE 4

The influence of calcium chloride and boric acid on release of bean pollen protoplasts in a dilute aqueous solution of sodium chloride plus sucrose was investigated. Bean pollen obtained as described in Example 1 was contacted with a 0.03M solution of sodium chloride (pH 6.0) containing 2.0% sucrose having varying quantities of calcium chloride and/or boric acid added to the solution.

The results are shown in Table 6. The degree of release varied when the concentration of either calcium chloride or boric acid, alone, was changed. Increasing boric acid from 50 ppm to 500 ppm to calcium chloride from 50 ppm to 400 ppm did not alter the total percentage of pollen grains that released protoplasts. However, the addition of either compound altered the ratio of totally free to partially free protoplasts. In the absence of calcium, up to 50 ppm boric acid had no apparent influence on the release of protoplasts by the dilute salt solution. Almost all were entirely free. With the addition of 100 to 200 ppm boric acid, only about 70% of the released protoplasts were entirely free. The number of entirely free protoplasts was significantly reduced from the control with the addition of 50 ppm calcium chloride in the absence of boric acid and were essentially eliminated at 300 ppm. When calcium chloride and boric acid were used together at low concentrations (50 and 25 ppm, respectively), almost all released protoplasts were free. As calcium chloride was increased to 100 ppm, or higher, only a few protoplasts were entirely free.

TABLE 6

| CaCl$_2$ (ppm) | H$_3$BO$_3$ (ppm) | Protoplast Release (%) | | |
|---|---|---|---|---|
| | | Total | Free | Partial |
| 0 (Control) | 0 | 86ax[1] | 82ax | 4dy |
| 0 | 50 | 85ax | 81ax | 4dy |
| 0 | 100 | 90ax | 63cy | 27cz |
| 0 | 200 | 86ax | 62cy | 24cz |
| 50 | 0 | 85ax | 70by | 15dz |
| 100 | 0 | 90ax | 30dz | 60by |
| 300 | 0 | 85ax | 3ey | 82ax |
| 500 | 0 | 85ax | 0ey | 85ax |
| 50 | 25 | 85ax | 77ay | 8dz |
| 100 | 25 | 87ax | 2ey | 85ax |
| 300 | 25 | 90ax | 1ey | 89ax |
| 100 | 50 | 90ax | 2ey | 88ax |
| 100 | 100 | 85ax | 3ey | 82ax |
| 300 | 100 | 88ax | 2ey | 86ax |

[1]Means in the same column followed by the same letter are not significantly different using the Duncan's Multiple Range test.

EXAMPLE 5

Gelatin (Fisher Scientific Company, Fair Lawn, N.J.) was placed in a graduated 100-ml Erlenmeyer flask. Where other additives were also used, they were added to the flask from a stock solution to obtain the desired concentration. Distilled water (100° C.) was added to the flask to reach a total volume of 100 ml. The mixture was stirred until dissolved. Approximately 10–12 cc of the medium was placed in a 300-mm diameter petri dish and the dish held at 150° C. until the gelatin solidified.

Pollen was used from tomato, green pepper (*Capsicum annuum*), cowpea, lima bean, and pea plants. Pollen was obtained as described in Example 1. Pollen from an individual flower was shaken onto the gelatin and the petri dish held at room temperature (ca., 23° C.) and at a relative humidity of approximately 98%. After 1 to 12 hours, released protoplasts were observed by the staining technique described above. Protoplasts were determined as total, free, or partial as described above. The results are shown in Table 7. As can be seen from the data, intact, viable protoplasts were obtained from all the plants treated.

TABLE 7

| Plant | Gelatin (%) | CaCl$_2$ (ppm) | H$_3$BO$_3$ (ppm) | Sucrose (%) | Protoplast Release (%) | | |
|---|---|---|---|---|---|---|---|
| | | | | | Total | Free | Partial |
| Tomato | 7 | — | — | — | 75 | 15 | 60 |
| | 8 | — | — | — | 55 | 2 | 53 |
| | 8 | — | 10 | — | 70 | 0 | 70 |
| | 8 | — | 50 | — | 82 | 0 | 82 |
| | 8 | — | — | 15 | 65 | 0 | 65 |
| | 10 | — | 50 | — | 60 | 10 | 50 |
| | 10 | — | 100 | — | 60 | 5 | 55 |
| Green Pepper | 7 | — | — | — | 75 | 40 | 35 |
| | 8 | — | 25 | — | 75 | 65 | 10 |
| | 8 | — | 50 | — | 80 | 75 | 10 |
| Cowpea | 5 | — | — | — | 82 | 0 | 82 |
| | 6 | — | 50 | — | 75 | 0 | 75 |
| | 7.5 | 300 | 100 | 10 | 65 | 0 | 65 |
| | 8 | — | 25 | — | 80 | 50 | 30 |
| Lima Bean | 8 | — | — | — | 35 | 3 | 32 |
| | 8 | — | 25 | — | 55 | 5 | 50 |
| | 8 | — | 50 | — | 80 | 10 | 70 |
| | 8 | — | 100 | — | 85 | 5 | 80 |
| | 12 | — | — | — | 55 | 0 | 55 |
| Pea | 6 | — | — | — | 20 | 0 | 20 |
| | 8 | — | — | — | 25 | 0 | 25 |
| | 8 | — | 50 | — | 82 | 8 | 74 |
| | 10 | — | 50 | — | 25 | 2 | 23 |

EXAMPLE 6

Gelatin and an osmolyte were used together in the aqueous medium to obtain intact, viable protoplasts. The aqueous medium was prepared as described in Example 5 except that instead of adding distilled water to the gelatin, the osmolyte in distilled water was used. Pollen was obtained as described in Example 1. After 12 hours, released protoplasts were observed by the staining procedure described above. The results are given in Table 8.

TABLE 8

| Plant | Additives | Protoplast Release (%) | | |
|---|---|---|---|---|
| | | Total | Free | Partial |
| Pea | 6% gelatin + 0.03M NaCl | 90 | 0 | 90 |
| Pepper | 1% gelatin + 0.03M NaCl | 75 | 70 | 5 |

It is understood that the foregoing detailed description is given merely by way of illustration and that modification and variations may be made therein without departing from the spirit and scope of the invention.

What is claimed is:

1. A method for obtaining intact, viable protoplasts from within the cell walls of mature pollen grains, comprising:

contacting a mature pollen grain having an inner protoplast and an outer cell wall with a pore, with an aqueous medium containing at least one additive of a type and in a concentration to cause the protoplast to expand and force it out through the pore in the cell wall of the pollen grain while maintaining the protoplast intact and viable, said medium being at a temperature and pH compatible with maintaining the viability of said pollen protoplast, wherein said method is carried out without a cell wall degrading enzyme.

2. The method of claim 1 which further comprises separating said intact, viable protoplast from said aqueous medium.

3. The method of claim 1 wherein said intact, viable protoplast is forced out of said pore and is entirely free of said cell wall.

4. The method of claim 1 wherein said intact, viable protoplast is forced partially out of said pore and is partially free of said cell wall.

5. The method of claim 1 wherein said protoplast expanding additive is an osmolyte.

6. The method of claim 5 wherein said osmolyte is a salt having a cation selected from the group consisting of sodium, potassium, and magnesium.

7. The method of claim 6 wherein said salt is at a concentration in the aqueous medium of 0.005 to 0.2M.

8. The method of claim 7 wherein said salt is at a concentration in the aqueous medium of 0.02 to 0.08M.

9. The method of claim 6 wherein the pH of the aqueous medium is 5 to 10 and the temperature is 1.65° C. to 38° C.

10. The method of claim 9 wherein the pH is 6 to 9 and the temperature is 10° C. to 27° C.

11. The method of claim 6 wherein said aqueous medium further contains agar in a concentration of 0.5 to 4.0%.

12. The method of claim 1 wherein said protoplast expanding additive is gelatin.

13. The method of claim 12 wherein said gelatin is at a concentration of 1 to 20%.

14. The method of claim 13 wherein said gelatin is at a concentration of 6 to 12%.

15. The method of claim 12 wherein the pH of the aqueous medium is 5 to 9 and the temperature is 20° C. to 30° C.

16. The method of claim 15 wherein the pH of the aqueous medium is 6 to 7 and the temperature is 23° C. to 27° C.

17. The method of claim 1 wherein said protoplast expanding additive comprises an osmolyte and gelatin.

18. The method of claim 1 wherein said aqueous medium further contains a protoplast stabilizer.

19. The method of claim 1 wherein said aqueous medium further contains a mineral salt in a concentration compatible with the viability of said protoplast.

20. The method of claim 1 wherein said pollen grain is obtained from *Phaseolus vulgaris* L.

21. The method of claim 12 wherein said pollen grain is obtained from the group consisting of cowpea, pea, tomato, lima bean, and pepper.

* * * * *